United States Patent [19]
Herbolzheimer et al.

[11] Patent Number: 5,157,054
[45] Date of Patent: Oct. 20, 1992

[54] CATALYST FLUIDIZATION IMPROVEMENTS (C-2546)

[75] Inventors: Eric Herbolzheimer, Annandale; Frederick J. Kaiser, Jr., Hanover Township, Morris County; Enrique Iglesia, Clinton, all of N.J.

[73] Assignee: Exxon Research and Engineering Company, Florham Park, N.J.

[21] Appl. No.: 660,198

[22] Filed: Feb. 25, 1991

Related U.S. Application Data

[63] Continuation-in-part of Ser. No. 504,745, Apr. 4, 1990, abandoned.

[51] Int. Cl.⁵ .................................................. C07C 1/04
[52] U.S. Cl. ................................................... 518/700
[58] Field of Search ........................................ 518/700

[56] References Cited

U.S. PATENT DOCUMENTS 2,662,091  1/1953  Odell .
4,788,222  11/1988  Rice et al. .
4,857,559  8/1989  Eri et al. .

OTHER PUBLICATIONS

Kolbel et al "Fisher-Tropsch Synthesis in the Liquid Phase," Catal Rev—Sci Eng. 21(2) 225-274 (1980).

*Primary Examiner*—Howard T. Mars
*Attorney, Agent, or Firm*—Jay S. Simon

[57] ABSTRACT

Three phase reactions are carried out in a slurry bubble column, e.g., hydrocarbon synthesis, wherein rising gas bubbles fluidize a catalytically active solid dispersed in a liquid phase and in the presence of at least one other solid different chemically or physically from the catalytically active solid.

21 Claims, 6 Drawing Sheets

CATALYST FLUIDIZATION IMPROVEMENTS (C-2546)

CROSS REFERENCE TO RELATED APPLICATION

This application is a continuation-in-part application of U.S. Ser. No. 504,745, filed Apr. 4, 1990 and now abandoned.

FIELD OF THE INVENTION

This invention relates to an improved method for conducting three phase reactions, that is, reactions involving the introduction of a fluidizing gas or liquid, preferably a gas, into a reactor containing catalyst particles and particles of at least one other solid, catalytic or inert, slurried in a liquid medium. In a preferred embodiment, this invention relates to hydrocarbon synthesis or Fischer-Tropsch processes wherein synthesis gas, hydrogen and carbon monoxide, is injected into or near the bottom of a bubble column which contains particles of a suitable hydrocarbon synthesis catalyst and particles of at least one other solid, catalytic or inert, slurried in a liquid medium, the mixing energy of the gas being sufficient to maintain the solids as a dispersion in the slurry liquid.

BACKGROUND OF THE INVENTION

Slurry phase reactions, particularly those occurring in bubble columns are well-known and need not be described here. Literature references for such systems are plentiful, for example, see Farley et al, The Institute of Petroleum, vol. 50, No. 482, pp. 27-46, February (1984); H. Storch, N. Columbis, R. B. Anderson, "Fischer-Tropsch and Related Synthesis", Wiley, 1951, New York; and J. Falke, "Advances in Fischer-Tropsch Catalysis, "Verlag, 1977, Berlin", as well as European Patent Application #88309904.6, publication no. 0313375.

Slurry phase reactions are often preferred over fixed bed processes because of easier heat removal in exothermic reactions and ease of contacting the reactants with the catalyst. Nevertheless, heat removal problems, for example, are not completely eliminated by changing from fixed bed to slurry phase processes. Often slurry phase reactions conducted in bubble columns require internal configurations for aiding heat removal in exothermic reactions, for improving contact between the reactants and the catalysts, and for preventing slumping of the bed, that is, where the catalyst particles accumulate near or settle at the bottom of the bubble column and inhibit both heat removal and reactant contacting, and otherwise affect the reaction deleteriously.

Slurry phase reactions, particularly those conducted in bubble columns can be improved dramatically by conducting the reaction in the presence of an additional solid material. The additional solid aids the fluidization of the primary catalytic material.

Catalyst particles in a bubble column tend to settle to the bottom of the column because of the influence of gravity and because of low liquid through-put rates typical of many slurry phase reactions. This settling tendency is opposed by dispersion forces created by rising bubbles of gas injected at or near the bottom of the reactor. Bubble column reaction conditions generally attempt to balance these opposing forces so that neither slumping of the catalyst bed nor carrying of the catalyst out of the column occurs. The balancing of these opposing forces results in an exponential distribution of the catalyst with the solids concentration decreasing by a factor of about 2.7 every time the vertical position in the reactor column is increased by an amount equal to the decay length, $D/U_s$, where D is the dispersion coefficient and $U_s$ is the settling velocity of the catalyst particles. The dispersion coefficient depends on the superficial gas velocity through the system and on the effective diameter of the reactor column. On the other hand, the settling velocity can be expressed as:

$$U_s = U_o(1-c)^n$$

where $$U_o = d_p^2 (\rho_s - \rho)g/18\mu$$

and wherein c is the volume fraction of solids in the slurry, $d_p$ is the particle diameter, $\rho_s$ is the density the solids, $\rho$ is the density of the slurry liquid, g is the gravitational constant, $\mu$ is the viscosity of the suspending liquid, and n is a constant ranging from 4-8. Hence, changing the solids concentration, for example, from 10% to 30% should decrease the settling velocity, and therefore, increase the decay length of the solids profile, by a factor of from 3 to 7.

Explained in other terms, a bubble column reactor—which for purposes of this invention is any reactor containing solids slurried in a liquid and into which gas (or another liquid) is injected or sparged into the column at or near the bottom of the column and gas bubbles rise in the column—allows a reaction to occur wherever there is catalyst. The dispersing force of the gas increases as the superficial gas velocity increases. Thus, as the superficial gas velocity increases from zero to any positive number, the catalyst instead of slumping to its minimum bed height will occupy an "expanded" bed height that depends on the gas velocity. Also, the expanded bed will have a concentration profile that depends on gas velocity, catalyst particle size, particle density and total loading of the catalyst. Additionally, if the fluidizing gas is a reactant, as in hydrocarbon synthesis reactions, less gas will be available higher in the column as the gas rises and reacts in the column.

The reaction taking place in the bubble column, whatever that reaction may be, will effectively and substantially take place within the expanded bed, i.e., where the catalyst is located. Now, by increasing the solids loading in the slurry, all other things being equal, the bed height will increase. Because the reaction, whatever it may be, takes place in the region of the expanded bed, the reaction zone is lengthened, also. The effects of increasing the reaction zone are manifold: more uniform reaction rate; more uniform heat release profile in the reactor (for exothermic reactions) or heat absorption (for endothermic reactions); less severe mass transfer limitations in the bottom portion of the reactor, thereby allowing better catalyst productivity, selectivity, and lower catalyst deactivation rates. Additionally, since heat release or absorption is more uniform, that is, the same amount of heat is released or absorbed, but over a longer distance resulting in a lower heat flux per unit volume, heat exchange surface areas can be distributed over a longer distance in the column thereby allowing reactor internals to be less expensive and easier to maintain. Increasing the solids loading has the additional effect of producing a lower volume fraction of gas per unit volume of reactor with the prospect for higher reaction rates per unit of reactor cross sectional area, and to increased thermal conductivity of the slurry; The latter effect further improving heat transfer.

SUMMARY OF THE INVENTION

Three phase reactors involving hydrocarbon-containing materials and wherein a first catalytically active particle or particles are slurried in a liquid phase, are carried out in an effective manner by conducting the reaction in the presence of particles of at least one other solid, and wherein gas bubbles from an injected gas provide substantially all of the energy required for maintaining the solids dispersed in the slurry liquid. For purposes of this invention, another solid is any particulate material other than the first catalytically active particle being used. In other words, the other solid or solids can be any particulate material to the extent it differs in any way from the catalytically active particle being used in the reaction. Thus, the other or second solid need only be different—chemically or physically—from the first solid. The material may be inert, e.g., porous or non-porous solids such as glass beads, inorganic oxides of Groups IIIB, IVB, VB, the lanthanides, and actinides, diatomaceous earths, kieselguhr, zeolites, or essentially any other solid, particulate material that is substantially inert at reaction conditions.

Additionally, the other solid may be catalytically active, for example, the same catalyst as the first catalytically active particle but of greater or lesser density, greater or lesser activity, productivity or selectivity; a different catalyst than the first catalytically active material but promoting the same general reaction (usually with slightly different results as in the difference in distillate yields when using supported cobalt or supported ruthenium in Fischer-Tropsch type reactions); a different catalyst than the first catalytically active material and having a different functionality, e.g., promoting a different reaction, such as a shift reaction or upgrading the product, for example, a zeolite that isomerizes olefins. Nevertheless, regardless of whether one or more reactions occur in the reactor, the result is that each reaction occurs in an expanded bed, that is, a catalyst zone greater than the catalyst zone if the additional solid or solids was not present.

Now, in any reactor wherein this invention will be applicable, the solids concentration profile of the first catalytically active solid will decrease from bottom to top. That is, the solids concentration per unit volume of reactor will be greater at the bottom of the reactor than at the top of the reactor. With the addition of another solid, whether inert or catalytically active, several factors need be considered:

If the second or other solid is of the same size and density as the first solid, that is, of the same buoyancy, the other solid will have the same concentration profile as the first solid but, of course, over an expanded bed;

If the second solid is of a greater density than the first solid, the bed expands and the second solid has a steeper concentration profile than the first solid, that is, at the bottom of the reactor the solids concentration per unit reactor volume will be greater for the second solid than the first solid and the reverse will be true at the top of the reactor;

If the second solid is of lesser density than the first solid, the bed expands and the second solid has a flatter concentration profile than the first solid, that is, at the bottom of the reactor the solids concentration per unit reactor volume will be lesser for the second solid than the first solid and the reverse will be true at the top of the reactor;

If the second solid is of greater size than the first solid an effect similar to that with a greater density particle will occur;

If the second solid is of lesser size than the first solid, an effect similar to that with a lesser density particle will occur.

The size of a particulate material usually refers to a mean size or average size because particulate materials, whether or not catalytic, are made up of particles having a size distribution. When used in this specification, particle size refers to mean particle size.

These factors are applicable, generally, and the settling velocity of a particle ultimately determines the concentration profile of that particle. As shown above, settling velocity is a function of particle diameter, particle density, slurry liquid density and viscosity, and volume fraction of solids in the slurry.

In fact, more than one additional solid may be added and depending on the relative density and size of each additional solid qualitative descriptions of the concentration profile of each solid vis-a-vis each other solid can be made based on the foregoing considerations. Additionally, quantitative descriptions of the concentration profile can be made based on the formula given above.

DETAILED DESCRIPTION

Figure 1:
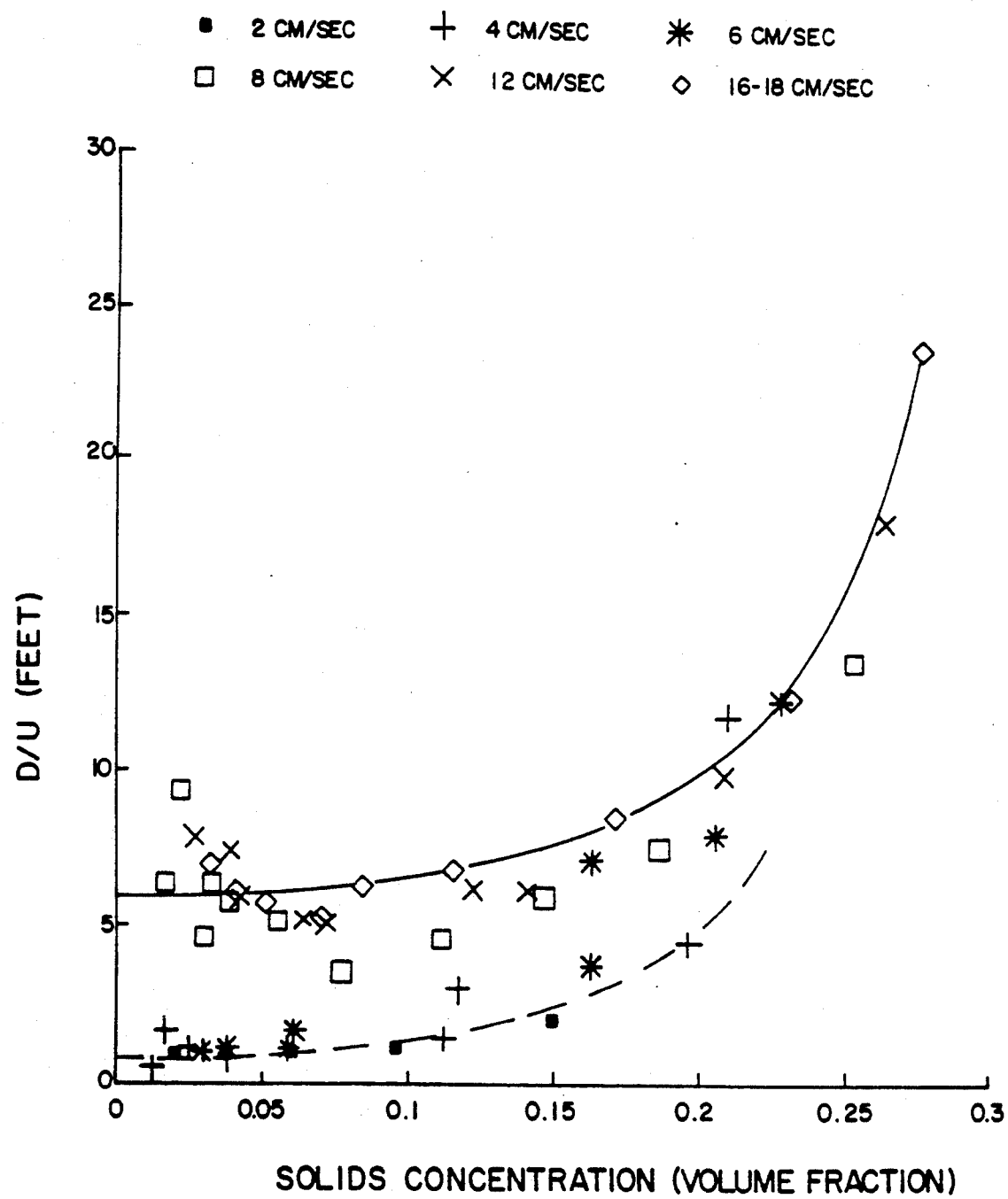
FIG. 1 is a plot of decay length vs. volume fraction solids concentration.

This invention will be described with reference to a preferred embodiment, that is, a hydrocarbon synthesis process wherein hydrogen and carbon monoxide are reacted in a bubble column wherein a hydrocarbon synthesis catalyst is slurried in a suitable organic liquid and the hydrogen and carbon monoxide are injected into the column at or near the bottom of the column. The products of the process are hydrocarbons, and is predominantly comprised of $C_{5+}$ hydrocarbons, preferably, $C_{10+}$ hydrocarbons.

In hydrocarbon synthesis processes carried out in slurry bubble columns, the catalyst is generally a particulate solid, e.g., cobalt or ruthenium, with or without a rhenium promoter, supported on a suitable carrier, e.g., silica, alumina, titania, zirconia, hafnia. This catalyst is then the first particulate solid. This invention contemplates conducting the hydrocarbon synthesis process in the presence of at least one other or second particulate solid, where "other" is defined above for purposes of this invention. The second solid has the effect of expanding the catalyst bed height and may be inert or it may be catalytically active for hydrocarbon synthesis or another, different reaction, preferably a reaction that complements hydrocarbon synthesis, e.g., isomerization with catalysts such as supported rhenium, nickel, or platinum, water-gas shift with catalysts such as bulk iron, copper, or chromium, olefin oligomerization (when the hydrocarbon product contains olefins) with catalysts such as zeolites, supported phosphoric acid, or any other reaction that can be conducted in a slurry bubble column using hydrocarbon synthesis products at essentially hydrocarbon synthesis reaction conditions.

Generically, a bubble column operates in a regime somewhere between plug-flow operation and fully backmixed or CSTR operation. In the plug-flow, backmixing is virtually eliminated by employing a fixed bed of catalyst or by having a very large L/d (where L and d are, respectively, the reactor length and effective diameter) ratio in a slurry reactor. Also, the concentration of (and partial pressure of) hydrogen and carbon monoxide decreases (as they convert) along the path of the reactor and the driving force for the reaction also decreases. Complete backmixing results in a concentration of (and partial pressure of) hydrogen and carbon monoxide that essentially corresponds to outlet conditions at every point in the reactor. Also, the driving force for the reaction is constant throughout the reactor and reflects the relatively low driving force at exit conditions.

Productivity is generally favored in plug-flow systems, and selectivity is favored in backmixed systems. Bubble columns while having attributes of both systems can be operated in either of these two extremes.

While specific definitions of a bubble column are difficult and the term covers a wide variety of reactors, one skilled in the art will have no difficulty in understanding that a bubble column has two basic attributes: (i) operation that is between that of a fully backmixed system and that of a plug flow system, and (ii) wherein a gas or gases are injected at or near the bottom of a reactor and rise in the form of bubbles through a liquid/solid slurry medium to the top of the reactor.

The slurry process of the present invention is advantageously carried out in the absence of liquid throughput. That is, substantially all, and preferably all of the energy necessary for maintaining the solids as a dispersion in the slurry liquid is provided by the injection of a gas, e.g., synthesis gas, at or near the bottom of the slurry reactor.

Figure 6:
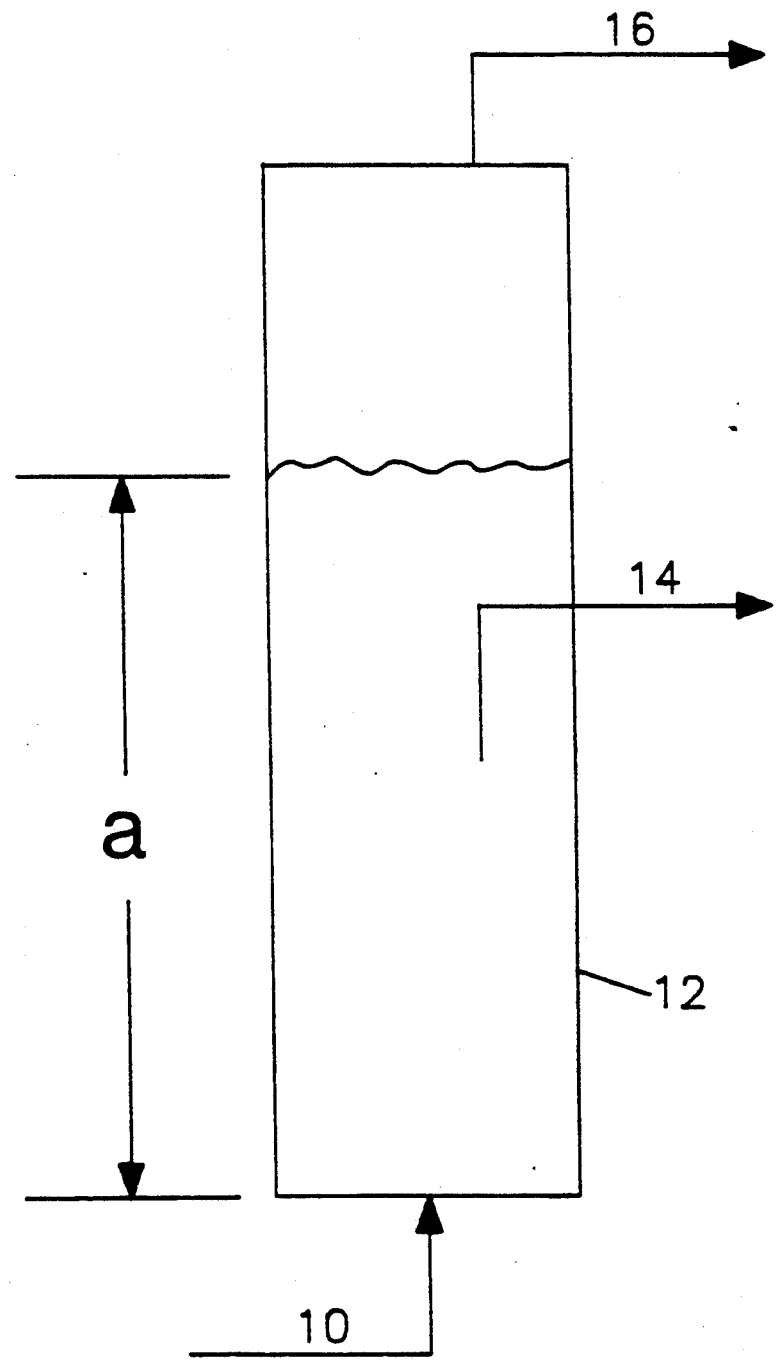
FIG. 6 is a generalized schematic of a slurry reaction in the absence of liquid recycle and in accordance with this invention.

In general, three phase slurry processes are carried out by providing a catalyst (and additional solid(s) as proposed by this invention) slurried in a liquid medium in a suitable reactor, see FIG. 6. A gas is injected (line 10) into the bottom of the reactor (12) causing gas bubbles to rise through the slurry zone (a) and buoy the solid particles therein. Liquid product, e.g., heavy hydrocarbons ($C_{5+}$) from a Fischer-Tropsch reaction are removed (line 14) through a filter element (not shown) located in the reactor and near the top of zone (a). Gaseous products (line 16) are removed from the top of the reactor. The liquid product is treated in necessary ways known to those skilled in the art and further processed. Slurry liquid is neither removed from the reactor nor is liquid product returned to the reactor. However, if for one reason or another, liquid is returned to the reactor, it is reinjected into the reactor at a point where it will provide little, preferably no, energy for buoying or dispersing the solids in the slurry liquid.

Hydrocarbon synthesis reactions are generally conducted at temperatures of about 150° C. to 300° C., preferably about 190° C. to about 260° C., and more preferably about 190° C. to about 240° C. Pressures may vary from about 0 to about 40 atmospheres, preferably above about 5 atmospheres, more preferably about 5 to 30 atmospheres, and still more preferably from about 10 to 25 atmospheres. Suitable hydrogen to carbon monoxide ratios are above about 0.5/1, preferably 1/1 to about 4/1, more preferably about 1.5/1 to about 3/1, and still more preferably about 1.7/1 to about 2.5/1. In a recently issued U.S. Pat. No. 4,681,867, hydrogen to carbon monoxide ratios of less than 1.0 were preferred. This invention can employ a broad range of hydrogen to carbon monoxide ratios and ratios closer to the stoichiometric consumption ratio are preferred. The stoichiometric ratio is about 2/1 for hydrocarbon synthesis and about 0.5 for combined hydrocarbon synthesis and water gas shift with an iron based catalyst.

Slurry reactions are well known and any process wherein a particulate catalyst is slurried in a liquid medium, the reaction being carried out in a bubble column, in the absence of liquid recycle (that is substantially all of the energy required for buoying the solid particles is provided by the rising gas), can be improved (and the bed height expanded) by this invention. Hydrocarbon synthesis processes are particularly preferred types of reactions, and particulate catalysts for this reaction have been widely reported and described in the literature.

Suitable hydrocarbon synthesis catalysts are particulate catalysts that can be slurried in a liquid medium and suspended in the liquid by the rising bubbles of the injected gas.

These catalysts have a catalytically active amount of a Group VIII non-noble metal deposited on a carrier, preferably an inorganic oxide support. The catalytic metal is preferably iron, nickel, cobalt, or the noble metal ruthenium. Iron, cobalt, and ruthenium are more preferred, cobalt and ruthenium most preferred, and cobalt still more preferred. The amount of the catalytic metal can vary rather widely depending on desired activity and the particular metal selected. Thus, ruthenium is sufficiently active at levels above about 0.3 wt %, while cobalt is sufficiently active at levels above about 2 wt %. Cobalt and other non-noble Group VIII metals are usually present in amounts ranging from about 5 to 45 wt %, preferably about 10 to 30 wt %.

Promoter metals may also be used to enhance the effect of the catalyst or to provide additional attributes such as the ability to regenerate the catalyst through air burning. Examples of promoter metals are rhenium, ruthenium, hafnium, zirconium, cerium, uranium, and titanium, preferably rhenium and hafnium, most preferably rhenium. Promoter metals are generally employed at lesser concentrations by weight than the primary catalytic metal. Usually an amount of promoter metal of at least 0.1/1 is sufficient relative to the catalytic metal.

Catalyst preparation is not critical, and catalysts can be prepared by a variety of methods, e.g., incipient wetness, impregnation, or spraying. The metal or metals are usually applied to the support as salt solutions either aqueous or organic. Suitable salt solutions are nitrates, carbonyls, acety-acetonates, and mixtures of the foregoing with or without water. Rhenium is often deposited from perrhenic acid. The metals, if more than one are employed, can be deposited but co-impregnation from suitable solutions is preferred.

After depositing the metals, the catalyst is usually dried at temperatures below about 125° C. Subsequently, the metals are frequently converted to their oxide form by calcining in oxygen or an oxygen containing gas at temperatures ranging from about 150° C. to about 500° C., preferably temperatures of about 150° C. to about 300° C. or directly reduced to the metal by the $H_2$ treatment described below. The active form of the catalyst is produced by converting the oxide to the elemental metal form by reducing in flowing hydrogen or a hydrogen containing gas at temperatures ranging from 150° C. to 500° C., preferably 150° C. to 300° C.

In operating a slurry reaction the particulate catalyst is slurried in a liquid medium. Generally, a total solids loading by volume of up to 50%, preferably about 10 to about 40% is employed. The particulate solids may range from powders to discreet particles, and are selected such that they are small enough to be maintained dispersed in the slurry liquid only through the mixing energy of the injected gas. For example from about 5 microns to about 1 mm, preferably about 10 microns to 200 microns, more preferably from about 20 microns to about 100 microns.

The slurry liquid used in the process is a liquid at the reaction temperature, must be relatively or largely or significantly chemically inert under the reaction conditions and must be a relatively good solvent for CO and hydrogen and possess good slurrying and dispersing properties for the finely divided catalyst. Representative classes of organic liquids which can be utilized are high boiling paraffins, olefins, aromatic hydrocarbons, alcohols, ethers, amines, or mixtures thereof. The high boiling paraffins include $C_{10}$-$C_{50}$ linear or branched paraffinic hydrocarbons; the olefins include polyolefin liquids; the aromatic hydrocarbons include $C_2$-$C_{20}$ single ring and multi and fused ring aromatic hydrocarbons; the ethers include aromatic ethers and substituted aromatic ethers where the ether oxygen is sterically hindered from being hydrogenated; the amines include long chain amines which can be primary, secondary, and tertiary amines, wherein primary amines preferably contain at least a $C_{12}$ alkyl group in length, secondary amines preferably contain at least two alkyl groups being $C_7$ or greater in length, and tertiary amines preferably contain at least three alkyl groups being $C_6$ or higher in length. The slurry liquid can contain N and O in the molecular structure but not S, P, As or Sb, since these are poisons in the slurry process. Representative examples of specific liquid slurry solvents useful are dodecane, tetradecane, hexadecane, octadecane, eicosane, tetracosane, octacosane, dotriacontane, hexatriacontane, tetracontane, tetratetracontane, toluene, o-, m-, and p-xylene, mesitylene, $C_1$-$C_{12}$ mono- and multi-alkyl substituted benzenes, dodecylbenzene, naphthalene, anthracene, biphenyl, diphenylether, dodecylamine, dinonylamine, trioctylamine, and the like. Preferred liquid hydrocarbon slurry solvents are octacosane or hexadecane. The most preferred solvents are hydrocarbon synthesis wax, i.e., the product of the Fischer-Tropsch reaction, and particularly $C_{20}$-$C_{40}$ hydrocarbon synthesis waxes.

In addition to CO hydrogenation, the improved process of the present invention can be applied to reactions such as hydrogenation, aromatization, hydrodesulfurization, hydrodenitrogenation, resid hydroprocessing, hydroformylation, hydroisomerization and related reactions. These are described in more detail in "Applied Heterogeneous Catalysis", J. F. LePage et al, Editions Tecnip, Paris (1987).

Product is removed from the bubble column, and if slurry liquid and catalyst are removed also, the latter are returned to the column by methods known in the art, involving either internal or external filtration, and at a point, as mentioned above, where the liquid does not contribute energy for maintaining the solids dispersed in the slurry liquid.

The data described in the examples was obtained in a 5 meter tall non-reactive bubble column with 15 cm internal diameter (i.e., then L/d ratio was greater than 20 corresponding to nearly plug flow reactor performance). Nitrogen gas was injected vertically into the column through a half inch hole at the bottom of a conical insert. This cone was used to insure fluidization of all the particles charged to the system. Pressure and temperature where monitored at 1 meter intervals along the column length. Slurry samples where also taken at these positions.

The liquid used was a paraffinic wax (predominantly $C_{20}$-$C_{40}$) which was produced in a slurry reactor via the Fischer-Tropsch process using a Co catalyst: The solid particles were either $TiO_2$ or glass beads. No liquid throughput was used.

EXAMPLE 1

Experimentally Determined Solids Decay Length

The solids distribution of 80 micron glass beads in Fischer-Tropsch paraffin wax ($C_{20}$-$C_{40}$) was determined in a 15 cm diameter, non-reactive bubble column by taking samples from the column at 1 meter intervals. The temperature was 400.F and the pressure was 280 psig for gas velocities below 8 cm/sec and 150 psig for gas velocities above 8 cm/sec. The decay length of the particle concentration profile was obtained by taking the slope of a line segment joining the data points when plotted as the logarithm of the solids concentration versus height. In FIG. 1, the decay length in each zone is plotted versus the average concentration in the zone for superficial gas velocities of 2–16 cm/sec.

The data can be correlated reasonably by:

$$D/U_s(feet) = 0.2(1 + 20c^2 + 3000c^4)/U_o(cm/sec) \text{ for } Ug < 4 \text{ cm/sec}$$

$$D/U_s(feet) = 1.2(1 + 3c^2 + 500c^4)/U_o(cm/sec) \text{ for } Ug > 8 \text{ cm/sec}$$

where $U_o$ is the Stokes settling velocity as defined above and c is the volume fraction of solids in the slurry. For intermediate velocities, a linear interpolation can be used. Note that increasing the solids concentration from 0.05 to 0.3 increases the fluidization height by a factor of 4–10 depending on the gas velocity. (See, also, R. H. Davis and Acrivos, Annual Review of Fluid Mechanics 17, 91, 1985.)

EXAMPLE 2

Method for Predicting Solids Distribution in a Slurry Bubble Column Reactor

The data of Example 1 allow predicting the catalyst distribution in a slurry bubble column reactor via the following algorithm. Suppose the reactor is charged with n species of particles each of which has a Stokes settling velocity $U_i$ and average concentration $C_{io}$. A given species may or may not be catalytic. The concentration of each species must satisfy the differential equation:

$$\frac{dc_i}{dx} = -U_i F(U_g, c) c_i$$

where x is the height from the bottom of the reactor, $F(U_g,c)$ is the function of $D/U_s$ given in Example 1, $U_g$ is the gas velocity at height x, and c is the local value of the total solids concentration (i.e., $c = \Sigma C_i$).

The algorithm begins by guessing the values of all the $c_i$'s at the bottom of the reactor and then the equations for the $c_i$'s are integrated numerically until the top of the slurry is reached. The gas velocity is computed by requiring a given overall conversion, X, and assuming the extent of reaction at any height is proportional to the fraction of the total catalyst inventory below that height; thus $$U_g = U_{go}[1 - X \int \Sigma c_i dx]$$

where $U_{go}$ is the gas velocity at the inlet and the sum is over the reactive solid species only.

When the integration reaches the top of the slurry, the total predicted inventory for each solid species is compared to the known charge; i.e., we check that $$C_{io} \int_o^H (1 - E) dx = \int_o^H (1 - E) c_i dx$$

where E is the volume fraction of gas (i.e., the gas holdup) at height x and H is the height of the slurry.

If these equalities are not satisfied, the assumed concentrations at the bottom of the reactor were not correct and they are adjusted using a Newton-Raphson iteration technique. The equations are then integrated starting from the new values, the iterations continuing until convergence is obtained.

This procedure can be easily extended to include the use of liquid flow along the reactor. The right hand side of the above equations are modified by subtracting the liquid velocity from the settling velocity of species i.

EXAMPLE 3

Effect of Adding Inert Solids

Figure 2:
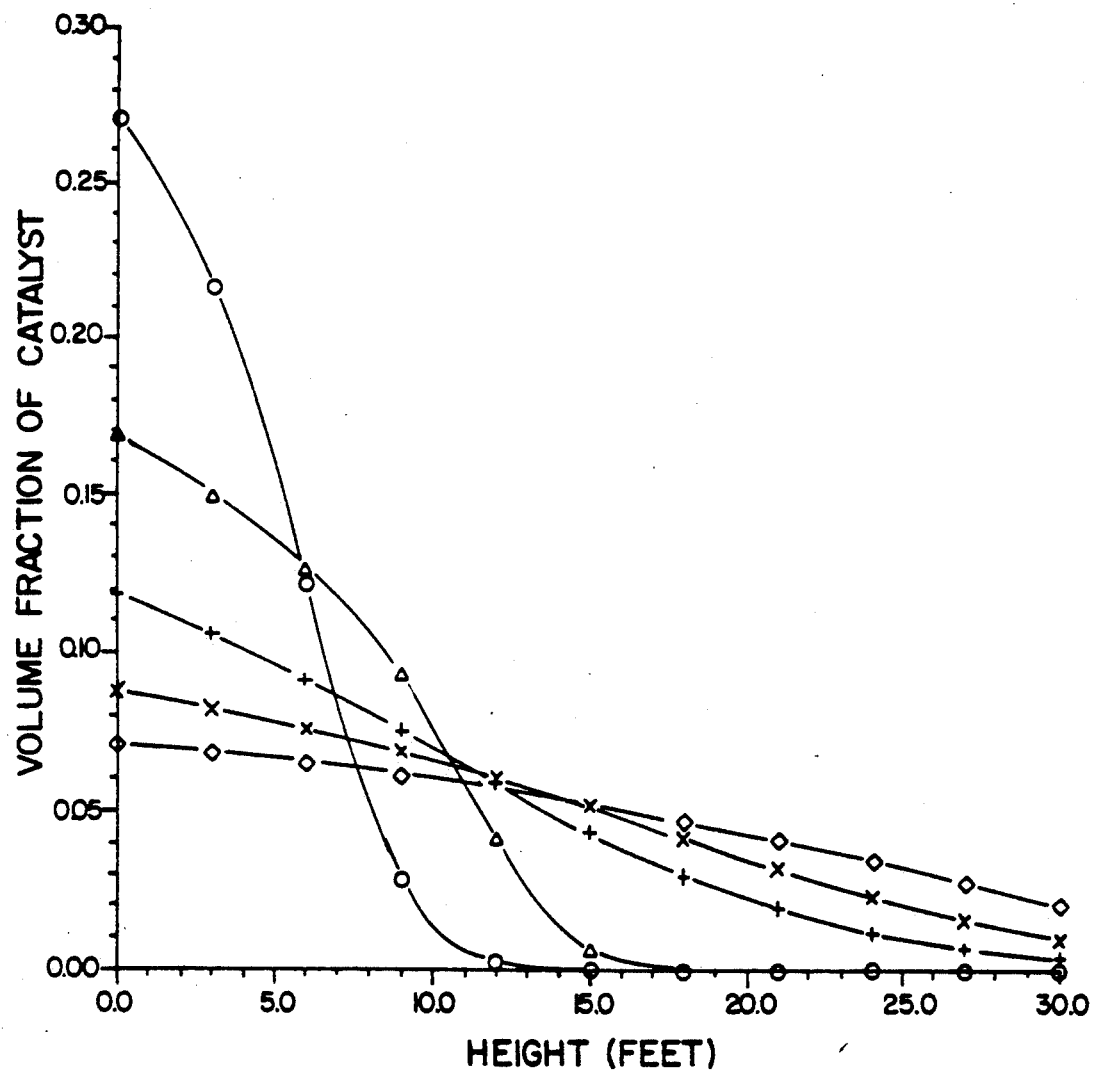
FIG. 2 is a plot of volume fraction vs. bed height when a second inert solid to a first catalytically active solid in a bubble column, the inerts being of the same density and diameter as the catalytic solid.

A computer model using the experimental data and correlations of Example 1 was developed (shown in Example 2) which predicts the solids distribution for a given charge of catalyst and inerts. In this example, the inerts are assumed to have the same density and diameter as the catalyst. Operating conditions were as in Example 1. The liquid viscosity and density are 0.9 cp and 0.7 g/cm$^3$, respectively, while the solids diameter and density are 50 micron and 2.7 g/cm$^3$, respectively. The average catalyst loading is 0.05 by volume on a gas-free basis and the expanded bed height is 30 feet. The gas velocity at the inlet is 8 cm/sec and the overall conversion (which determines the gas concentration) is 0.8. FIG. 2 shows the catalyst distribution with 0, 0.05, 0.1, 0.2, and 0.3 volume fraction of inert solids added.

FIG. 2 shows that with only catalyst, no additional solid, the effective bed height was about 13 feet. That is, all of the catalyst, at the operating conditions, was dispersed over about 13 ft. of the reactor and catalyst distribution was more highly concentrated in the lower part of bubble column. With 5 vol % inerts added to reactor, the bed expands to about 18 feet and while catalyst is still more concentrated in the lower part of the column, the concentration gradient is not nearly as steep as it is in the absence of additional solids.

Thus, the addition of a small amount of solids resulted in about a 38% increase in bed height. Further, virtually any addition of solids will result in a significant expansion of the bed. Bed expansions of at least 10% result in significant process improvement, e.g., heat transfer, and bed expansions of at least about 20% are preferred, more preferably 30%, still more preferably at least about 50%, and most preferably at least about 100%. Bed expansion is limited only by the physical height of the bubble column being used.

As more inert solids are added the bed further expands, to at least about 30 ft., and the concentration profile of the catalyst continues to flatten. Thus, the catalyst is now distributed over 30 ft. of bubble column as opposed to only 13 feet of bubble column when no inerts are added. Additionally, the concentration of catalyst in the lower portion of the bed is less when inerts are added than when the bed is free of additional solids. Thus, hot spots due to high concentrations of catalyst in the lower portion of the bed can be substantially minimized.

EXAMPLE 4

Effect of Slow Settling Inerts

This example is identical to Example 2 except the inerts are 1 micron in diameter and have a density of 2.7 g/cm$^3$ (the same as the catalyst). These solids are uniformly distributed and will pass through the filter.

FIG. 3 shows, again, that without any additional solids, the bed height is about 13 feet and the catalyst profile is rather steep, with most of the catalyst at the bottom of the column. When 5 vol % inerts of similar density as the catalyst but of micron diameter, the bed expands to about 18 feet and the catalyst profile changes, the catalyst being distributed over a greater bed height. Similar effects are obtained when up to 30 vol% of inerts of 1 micron diameter are added. The results obtained are similar to those shown in FIG. 1, the volume fraction catalyst being slightly higher in the lower portion of the bed than when the same size, same density particle was added.

EXAMPLE 5

Effect of Fast Settling Solids

The conditions in this example are the same as in Example 1 except the inert solids are added with 0.20 average volume fraction with a 100/0, 50/50, and 0/100 split of 100 micron and 1 micron diameters. The larger solids go preferentially to the bottom of the reactor and displace more catalyst while the smaller solids are uniformly distributed and help to fluidize the catalyst in the upper portion of the reactor. Because of their size, the large particles can be easily filtered from the product stream while the small ones can pass freely through the filter and can be removed from the product stream outside of the reactor.

Figure 3:
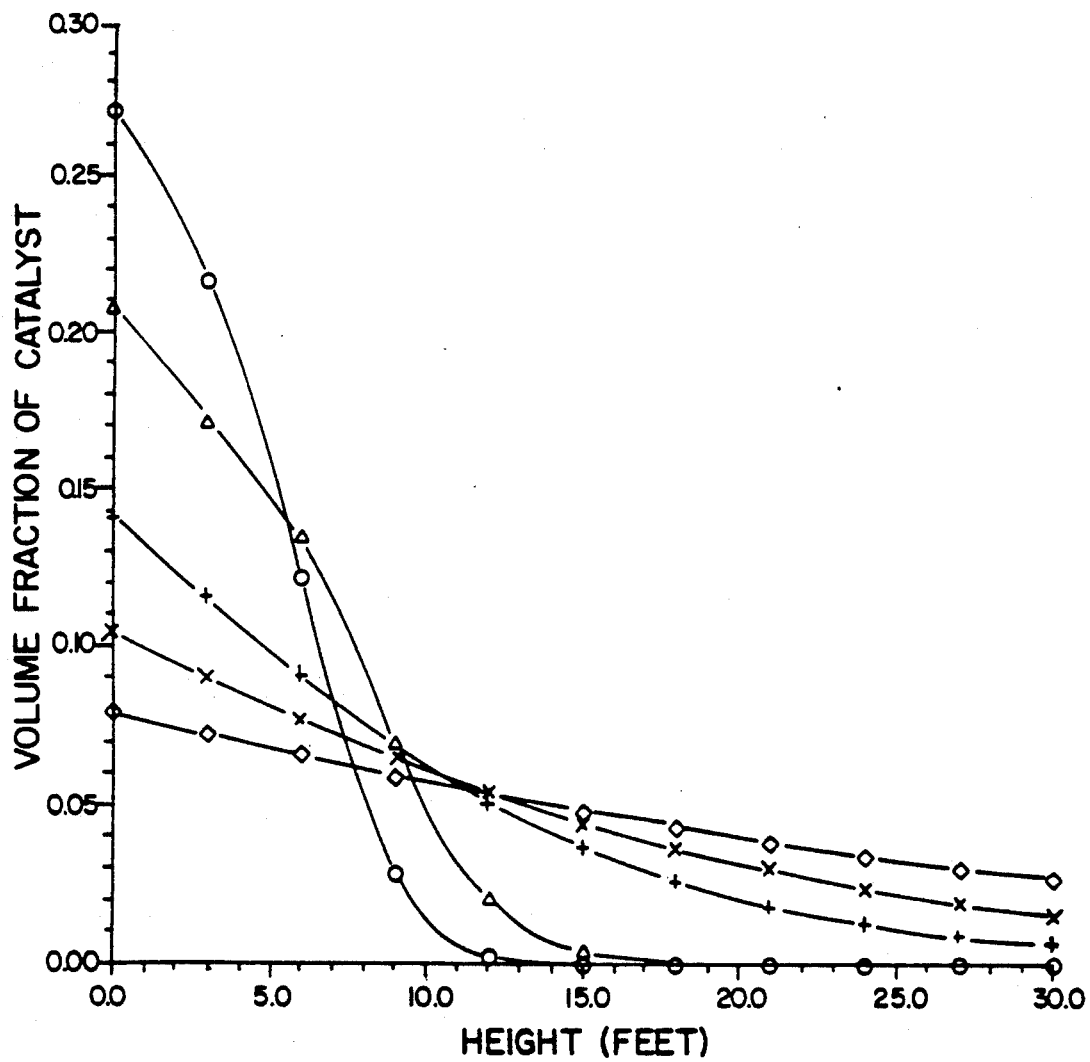
FIG. 3 is a plot of volume fraction of catalyst vs. bed height for adding a second, inert solid of the same density as the first catalytically active solid but having a 1 micron diameter.
Figure 4:
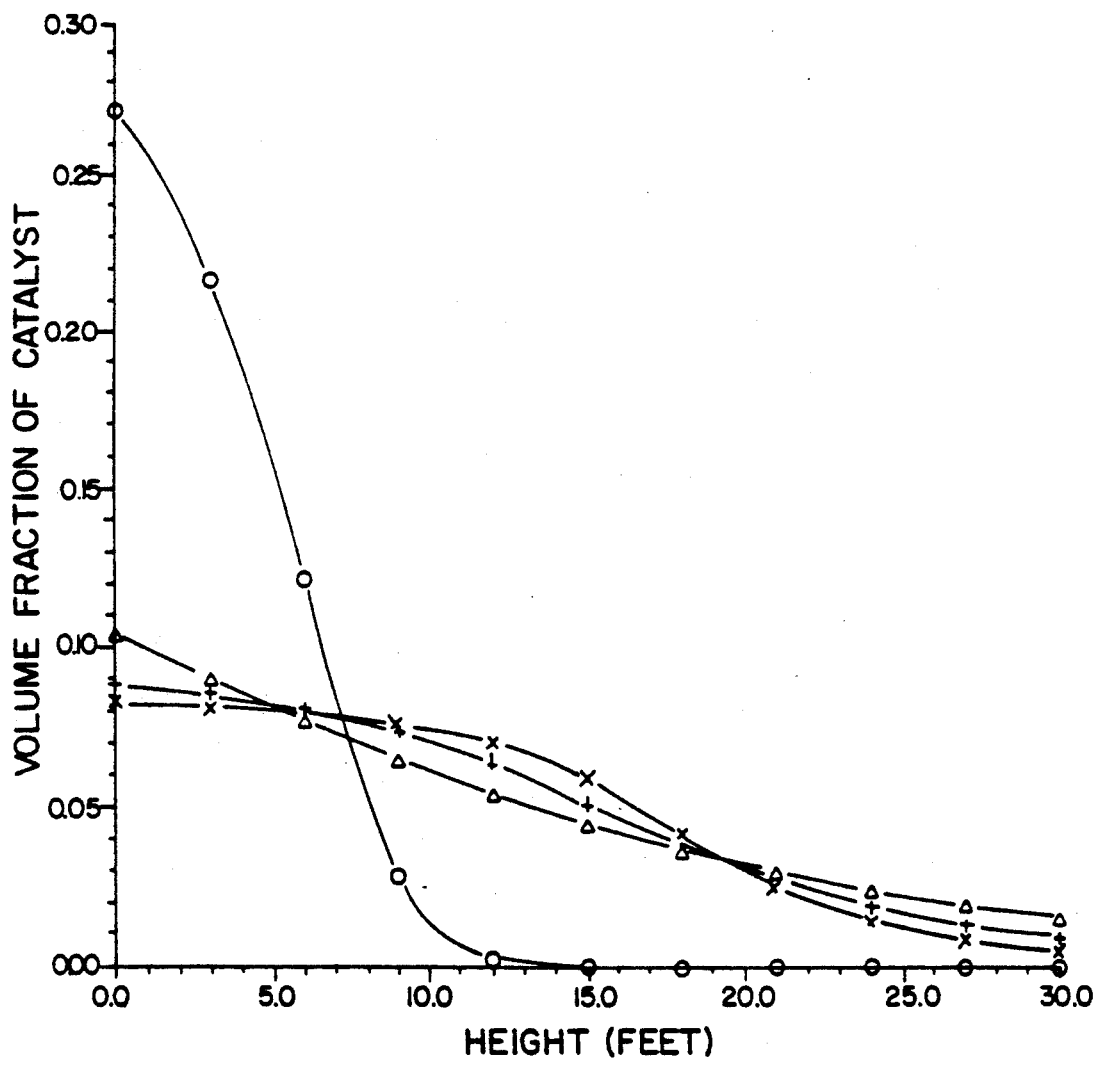
FIG. 4 is a plot of volume fraction of catalyst vs. bed height for adding a second inert solid of the same density of the first catalytically active solid but having particle diameters of 1 micron and 100 microns.

FIG. 4 shows the same catalyst volume concentration as in FIGS. 2 and 3 when no additional solids are added. However, when 20 volume % average of additional particles of 100 microns and 1 micron are added, the bed again expands to at least about 30 ft., or about 2.5 times the original bed height.

EXAMPLE 6

Effect of Higher Catalyst Loading on Catalyst Distribution

Figure 5:
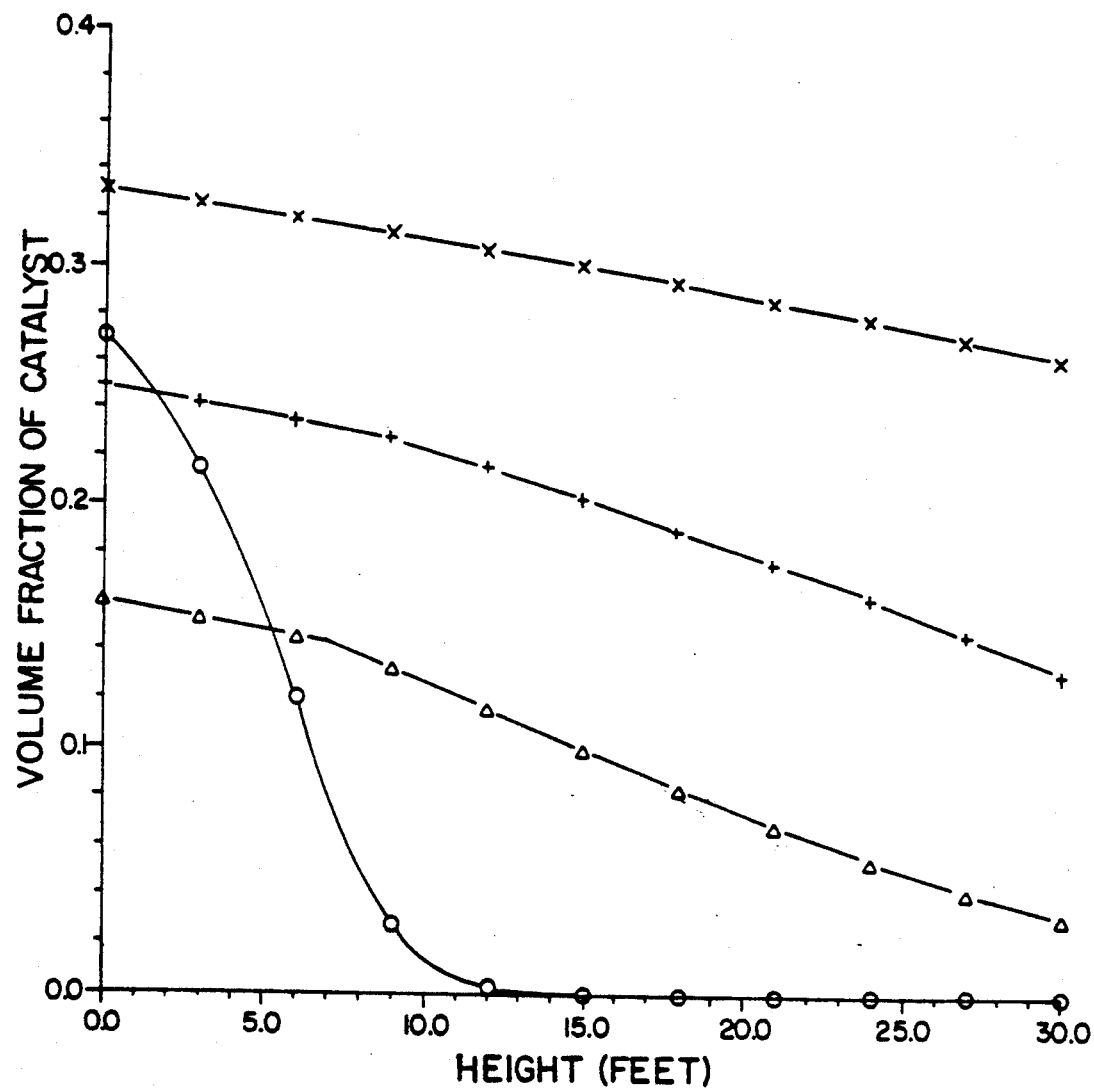
FIG. 5 is a plot of volume fraction of catalyst v. bed height when adding a second solid of lower activity to a first catalytically active solid in a bubble column.

The computer model, coupled with the correlations and conditions in Example 1, was used in determining the solids distribution for a given catalyst charge. In this example, the reactor inlet gas velocity was 8 cm/sec with a bed height of 30 ft. and the effect of decreasing the catalyst activity while increasing the loading to maintain the same overall conversion was determined. The liquid viscosity and density are 0.9 cp and 0.7 g/cm$^3$, respectively. The diameter of the catalyst pellets is 50 microns. The density of the most active catalyst is 2.7 while that in the lower activity cases is taken as 1.0. In Figure 5, the effect on the catalyst distribution is shown when the original activity is decreased by factors of 2, 4, and 6. Hence, using a larger amount of a less active (potentially less expensive) catalyst has benefits in increasing the bed height).

What is claimed is:

1. A slurry phase hydrocarbon synthesis process for the conversion of hydrogen and carbon monoxide at reaction conditions to products which comprises
   injecting a gas comprising hydrogen and carbon monoxide at or near the bottom of a bubble column containing a slurry liquid, a catalytically active first solid and at less a second solid, dispersing the solids in the slurry liquid, all of the energy therefor being supplied by the gas, in the absence of liquid product recycle, the amount of the second solid being sufficient to increase the bed height of the first catalytic solid by at least 10%, and
   recovering liquid product.

2. The method of claim 1 wherein the second solid is inert.

3. The method of claim 1 wherein the second solid is catalytically active.

4. The method of claim 1 wherein the second solid is of equivalent buoyancy as the catalytic solid.

5. The method of claim 1 wherein the second solid is of greater density than the catalytic solid.

6. The method of claim 1 wherein the second solid is of lesser density than the catalytically active solid.

7. The process of claim 1 wherein the first solid comprises cobalt or ruthenium and a carrier therefor.

8. The process of claim 1 effected in the absence of slurry liquid recycle.

9. The process of claim 1 wherein the catalytically active solid comprises cobalt or ruthenium.

10. The process of claim 9 wherein the cobalt or ruthenium is supported on a carrier.

11. The process of claim 10 wherein the carrier comprises a predominant amount of titania.

12. The process of claim 11 wherein a promoter is present.

13. The process of claim 12 wherein the promoter is selected from the group consisting of rhenium, ruthenium, hafnium, cesium, uranium and titanium.

14. The process of claim 13 wherein the promoter is rhenium.

15. A slurry phase hydrocarbon synthesis process for the conversion of hydrogen and carbon monoxide, at reaction conditions, to liquid products which comprises
    injecting a gas comprising hydrogen and carbon monoxide at or near the bottom of a bubble column reactor containing a slurry liquid, a catalytically active first solid comprising cobalt or ruthenium and at lest a second solid, dispersing the solids in the slurry liquid, all of the energy therefor being supplied by the gas, and in the absence of liquid product recycle, the amount of the second solid being sufficient to increase the bed height of the first catalytic solid by at least about 20%, and
    recovering liquid product.

16. The process of claim 15 wherein the liquid product comprises C$_5$+ hydrocarbons.

17. The process of claim 15 wherein the second solid is inert.

18. The process of claim 15 wherein the other solids are present in an amount of at 10 vol % based on total solids.

19. The process of claim 15 wherein the other solids are present in an amount of at least 30 vol % based on total solids.

20. The process of claim 15 wherein the second, other solid is a hydrocarbon synthesis catalyst of different density than the first solid.

21. The process of claim 15 wherein the second, other solid is a hydrocarbon synthesis catalyst of different size than the first catalytic solid.

* * * * *